United States Patent [19]

Daniher et al.

[11] 4,146,557

[45] Mar. 27, 1979

[54] ADDITION OF N,N-DICHLORO-N-ACYL COMPOUNDS TO CONJUGATED DIENES AND SULFONAMIDE PRODUCTS THEREFROM

[75] Inventors: Francis A. Daniher, Alma, Mich.; Alexis A. Oswald, Mountainside, N.J.

[73] Assignee: Exxon Research & Engineering Co., Florham Park, N.J.

[21] Appl. No.: 579,455

[22] Filed: May 21, 1975

Related U.S. Application Data

[63] Continuation-in-part of Ser. No. 688,308, Dec. 6, 1967, Pat. No. 3,884,963.

[51] Int. Cl.$^2$ ............................................. C07C 125/06
[52] U.S. Cl. ................................. 260/556 N; 424/314; 424/300; 560/115; 560/161; 560/30; 560/12; 260/404; 260/465.4; 260/556 A; 260/556 N; 260/556 AR; 260/556 B; 260/556 C
[58] Field of Search ........ 260/556 A, 556 N, 556 AR, 260/556 B, 556 C; 424/300, 314; 560/115, 161

[56] References Cited

PUBLICATIONS

Daniher & Butler, The J. of Organic Chem., vol. 33, #12, pp. 4336–4340.

*Primary Examiner*—Paul J. Killos
*Attorney, Agent, or Firm*—Joseph J. Allocca

[57] ABSTRACT

N,N-dichloro-N-acyl compounds, such as N,N-dichlorocarbamates, sulfonamides and amidosulfonamides selectively react with conjugated dienes to yield the corresponding 1,4-adducts, i.e. N-chloro-N-chlorocrotyl compounds. The N-chloro group of these adducts can be selectively reduced by aqueous sodium sulfite. Both the original and the reduced adducts are novel compositions useful as biologically active compounds and vulcanizing agents. The N-chlorocrotyl sulfonamides and their N-chloro derivatives are particularly claimed compositions.

17 Claims, No Drawings

ADDITION OF N,N-DICHLORO-N-ACYL COMPOUNDS TO CONJUGATED DIENES AND SULFONAMIDE PRODUCTS THEREFROM

CROSS-REFERENCE TO RELATED APPLICATION

This application is a continuation-in-part of U.S. Ser. No. 688,308, now U.S. Pat. No. 3,884,963 filed Dec. 6, 1967.

THE INVENTION

The present invention relates to a novel, selective diene addition process resulting in new, useful carbamates heretofore unavailable in the art. More particularly, this invention describes the selective addition of N,N'-dichloro-acyl compounds, such as N,N-dichlorocarbamates, N,N-dichlorosulfonamides, N,N-dichloroamidosulfonamides to conjugated dienes yielding N-chlorocrotyl acyl compounds.

N-Acyl compounds such as carbamates and sulfonamides are a known useful class of compounds. For example, carbamates or urethanes are a widely known type of compounds. Some of them are extremely useful in the pesticide, pharmaceutical and polymer industry. The importance of selected members of N-acyl compounds has stimulated interest in new types of carbamates, sulfonamides and amidosulfonamides and novel methods of preparing such compounds.

The addition of N-chloro dialkylamines to a conjugated diene, 1,3-butadiene was reported to occur in acidic medium to yield up to 60% of the corresponding 1,4-adducts (R. S. Neale and R. L. Hinman, J. Am. Chem. Soc. 85, 2666 (1963)).

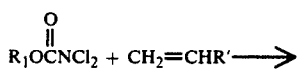

$$R_2NCl + CH_2=CH-CH=CH_2 \xrightarrow{H_2SO_4}{HOAC}$$

$$R_2NCH_2CH=CHCH_2Cl$$

The addition of N,N-dichlorocarbamates to a variety of monoolefins has been recently reported to yield the corresponding anti-Markovnikov adducts in yields generally ranging from 25–65%. (One high yield exception was the addition to styrene where an 80% yield was obtained):

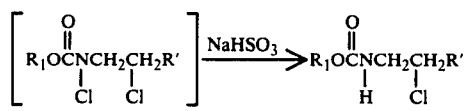

In the present invention, it has been found surprisingly that the addition of N,N-dichlorocarbamates to 1,3-butadiene in neutral media gives a quantitative yield of the corresponding adducts in a spontaneous reaction.

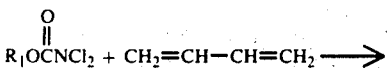

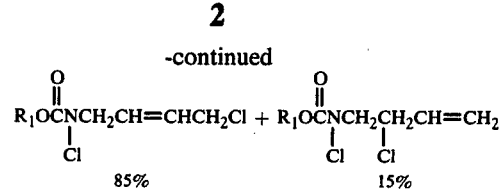

85%    15%

Characteristic of the addition to 1,3-butadiene and other conjugated dienes, in the $C_4$ to $C_{30}$ carbon range, preferably $C_4$–$C_6$, is the fact that the predominant mode of addition to the diene is 1,4-addition without formation of diaddition products to the diene.

Similarly, one mole of a difunctional carbamate reacts in the same manner with two moles of a conjugated diene as per the following equation: e.g.,

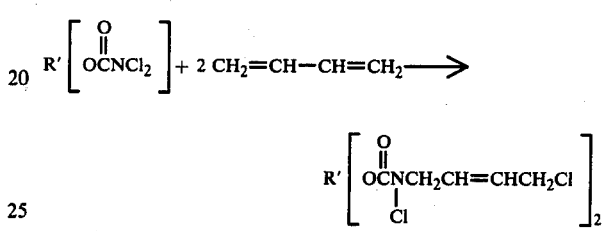

The resulting N-chloro-N-chlorocrotyl carbamates could be reduced by sodium sulfite to yield a surprisingly high yield of the corresponding N-chlorocrotyl carbamate, e.g.,

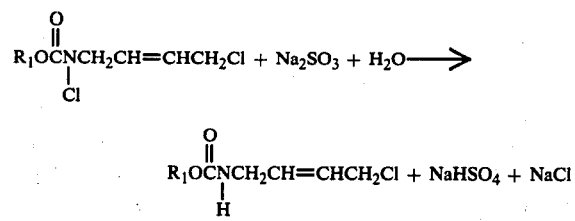

The reduction of the N-chloro group of carbamates with sodium hydrogen sulfite is a known process. It was found that for the reduction of our chlorocrotyl carbamate adducts the use of sodium sulfite is much preferable.

The addition of other N,N-dichloro acyl compounds, such as N,N-dichloro sulfonamides and N,N-dichloro dialkylamidosulfonamides to conjugated dienes was also found to occur with a surprising ease and selectivity as shown for butadiene additions by the following reaction equations:

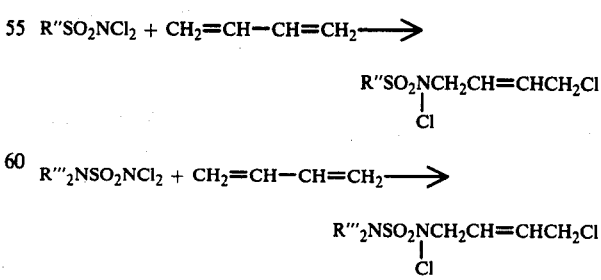

These N-chloro-N-chlorocrotyl adducts can be again advantageously reduced by sodium sulfite to the corresponding N-chlorocrotyl compounds:

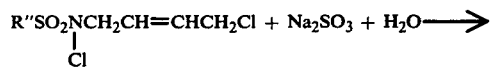

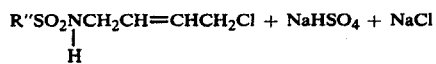

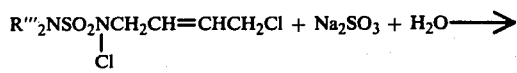

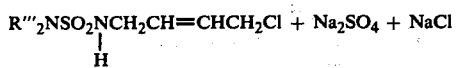

The above addition and reduction processes lead to novel types of acyl compounds as shown by the following reaction scheme:

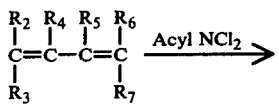

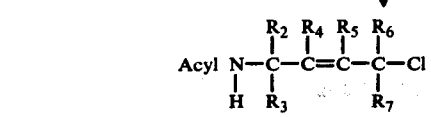

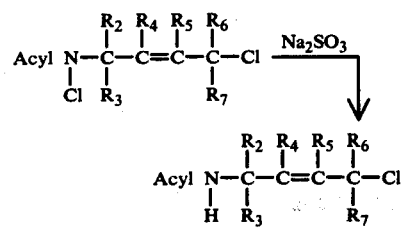

wherein Acyl is an acyl group in the $C_1$ to $C_{30}$ carbon range preferably $C_1$ to $C_6$, such as carboalkoxy, R'OCO, hydrocarbyl sulfonyl R"SO$_2$, dialkylamidosulfonyl, (R''')$_2$NSO$_2$; R$_2$ to R$_7$ are hydrogen, chlorine, fluorine, an alkyl group having from 1 to 30 carbon atoms such as methyl, ethyl, propyl, isopropyl, butyl, isobutyl, heptyl, decyl, dodecyl, tridecyl, hexadecyl, eicosyl, etc., preferably 1 to 5 carbon atoms; substituted alkyl where the substituents are selected from the group consisting of halo, nitro, sulfone, —CO$_2$R; aryl having from 6 to 10 carbon atoms such as phenyl; substituted aryl such as aralkyl, including benzyl, beta-phenethyl, and other substituted forms of aryl wherein the substituents are selected from the group consisting of halo, nitro, carboxyl, CO$_2$R, etc., phenyl and substituted phenyl having 6 to 10 carbon atoms such as nitrophenyl, chlorophenyl, xylyl, etc.

More particularly, the addition of N,N-dichloro carbamates, i.e. dichlorourethanes to conjugated dienes and the reduction of the resulting monoadducts yields the following types of novel compositions:

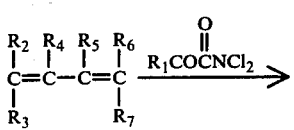

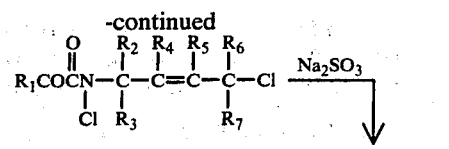

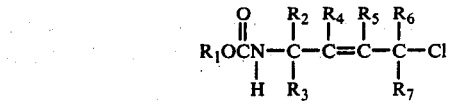

wherein R$_2$ to R$_7$ are the same as previously defined. R$_1$ is an alkyl or substituted alkyl group having from 1 to 30 carbon atoms such as a simple alkyl group exemplified by methyl, ethyl, isopropyl, tertiary butyl, dodecyl, hexadecyl, etc. and a substituted alkyl group wherein the substituents are selected from the group consisting of halo, nitro, sulfone, carboxylic ester having 2 to 6 carbon atoms, etc.

Bis-N,N-dichloro carbamates can be also added to conjugated dienes to yield the following novel compositions:

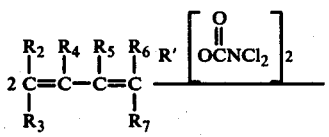

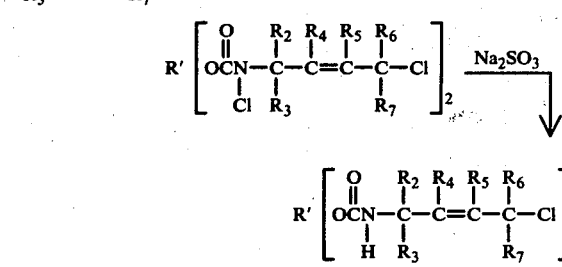

wherein R$_2$ to R$_7$ are the same as previously described, R' is a bivalent alkylene or substituted alkylene radical having from two to twelve carbon atoms such as ethylene, hexamethylene, xylylene, etc., preferably 2 to 6 carbon atoms.

Furthermore, the addition of N,N-dichloro sulfonamides to conjugated dienes specifically produces novel monoadducts which can be reduced with sodium sulfite as shown in the following:

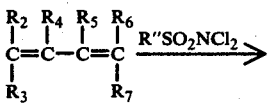

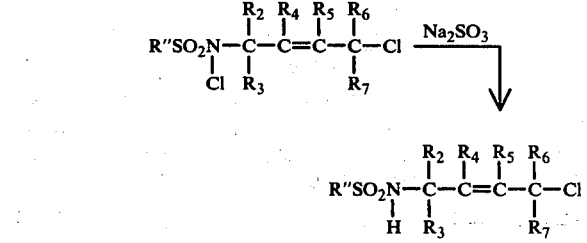

wherein R$_2$ to R$_7$ are the same as previously defined, R" is a hydrocarbyl or a substituted hydrocarbyl having 1 to 30 carbon atoms such as methyl, hexadecyl, trichloromethyl benzyl, phenyl, methylsulfonylphenyl, chlorophenyl, trichlorophenyl, nitrophenyl, naphthyl, tolyl, chlorotolyl, etc.

The invention specifically includes the compounds derived by the addition of N,N-dichloro N',N'-dialkyl sulfamides to conjugated dienes and by the subsequent reduction of the adducts:

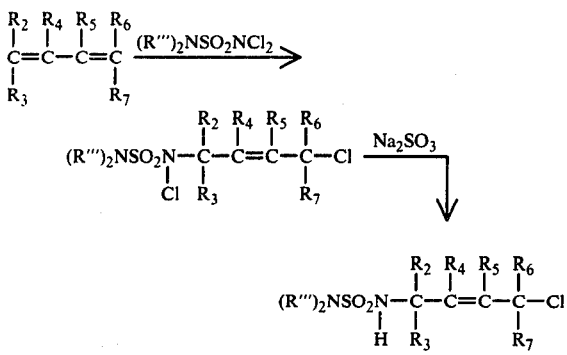

wherein $R_2$ to $R_7$ are the same as previously defined, $R'''$ is an alkyl group having from one to thirty carbon atoms such as methyl, isopropyl, hexadecyl.

The novel reactions described in the present invention produce the following types of novel compositions:

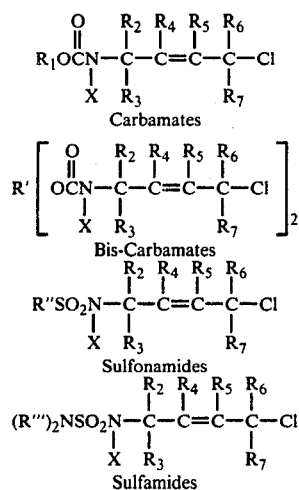

wherein $R_2$ to $R_7$, $R_1$, $R'$, $R''$, $R'''$ are as previously defined and X is selected from the group consisting of chlorine and hydrogen. In the pesticide and medicinal compositions of the present invention, X is chlorine and hydrogen while in the vulcanization additives X is always chlorine.

In a preferred embodiment of this invention, N,N-dichloro acyl compounds can be reacted with 1,3-butadiene at low temperatures, e.g. between $-10°$ and $+20°$ C. Other conjugated dienes may be used in the $C_4$ to $C_{30}$ carbon range preferably $C_4$ to $C_6$ carbon range. The preferred dienes include isoprene, 1,3-butadiene; chloroprene; 1-phenyl butadiene, 1,4-diphenylbutadiene; 2,3-dimethylbutadiene; piperylene; 2,3-dichloro-1,3-butadiene; 2-ethyl-1,3-butadiene; 1,3-hexadiene; 2,4-hexadiene; 2-methyl-1,3-pentadiene; 4-methyl-1,3-pentadiene. Other, less preferred, dienes that are suitable for use in this invention include 1,3-cyclohexadiene; 1-chloro,1,3-butadiene; cyanoprene; fluoroprene,1,3-cyclo-octadiene; 2,5-dimethyl-2,4-hexadiene; cyclopentadiene, etc. The foregoing enumeration of dienes is merely intended to be a representative, and not exhaustive, listing of dienes suitable for application within the scope of this invention.

As N,N-dichloro acyl compounds, N,N-dichloro carbamates may be used. Examples of suitable N,N-dichlorocarbamates are the following: N,N-dichloroethyl carbamate, N,N-dichlorohexadecyl carbamate, N,N-dichloro-i-propyl carbamate, N,N-dichlorocyclohexyl carbamate, N-N-dichloro-2-chloroethyl carbamate, N,N-dichloro-2-nitroethyl carbamate, N,N-dichlorotrifluoroethyl carbamate, N,N-dichloromethylsulfonylethyl carbamate, N,N-dichlorotrichloromethyl carbamate, N,N-dichlorocarbomethyloxyethyl carbamate, N,N-dichlorobenzyl carbamate. Any alkyl or substituted alkyl ester of N,N-dichlorocarbamic acid can be used as a starting material as long as the alkyl portion does not contain any sutstituent which would react with the N,N-dichlorocarbamate group. For example, vinyl-, mercapto-, or amino- substituted dichloro carbamates would not be suitable.

Suitable bis-N,N-dichloro carbamate reactants include ethylene bis-N,N-dichloro carbamate, hexamethylene N,N-dichloro carbamate, p-xylylene N,N-dichloro carbamate, etc.

Another class of N,N-dichloro acyl compound reactants consists of N,N-dichloro sulfonamides. Suitable N,N-dichloro sulfonamides are exemplified by the following: N,N-dichloro methanesulfonamide, N,N-dichloro trichloromethanesulfonamide, N,N-dichloro chloroethanesulfonamide, N,N-dichloro dodecane sulfonamide, N,N-dichloro benzenesulfonamide, N,N-dichloro 4-chlorobenzenesulfonamide, N,N-dichloro 2,4,5-trichlorobenzene sulfonamide, N,N-dichloro 4-toluenesulfonamide, N,N-dichloro 2-naphthalenesulfonamide.

A third class of N,N-dichloro acyl compounds which can be added to conjugated dienes according to the present invention is represented by N,N-dichloro amidosulfonamides. Suitable N,N-dichloro dialkyl amidosulfonamides are N,N-dichloro dimethylamidosulfonamide, N,N-dichloro diisopropylamidosulfonamide, N,N-dichloro dihexadecylamidosulfonamide.

In general, any N,N-dichloro acyl compound will add to conjugated dienes under appropriate conditions. With liquid and gaseous reactants the reaction is usually carried out in the absence of solvents at low temperatures. Solid reactants such as higher molecular weight N,N-dichloro carbamates and dienes may require elevated temperatures or suitable solvents to satisfactorily effect reaction.

The general reaction conditions that may be utilized in the addition process of this invention comprise temperatures ranging from about $-80°$ to about $100°$ C., preferably from about $-20°$ to about $+30°$ C. The reaction time is dependent upon the rate of addition and it may vary from spontaneous reaction to about 8 hours, depending upon the choice of reactants and the reaction conditions but may take as long as about 24 hours, assuming proper mixing of reactants. Ordinarily, however, the reaction should take no longer than about one hour.

Pressures ranging from 1 to 10 atmospheres can be used. Preferably, however, the reaction is conducted at atmospheric pressure.

Preferably, the ratio of reactants is equimolar; however, excess diene can be used. In general, the ratio of reactants can vary from 1:1 to about 5:1 moles of diene per mole of N,N-dichloro acyl compound. While an excess of N,N-dichloro compound could be used, this is not at all preferred since any excess of this reactant constitutes a waste thereof. From the previous equations, it is manifest that, with a difunctional carbamate, a minimum of two moles of the diene reactant is required.

Various solvents useful in the foregoing process, preferably inert solvents, include such solvents as paraffinic and aromatic hydrocarbons and their halo derivatives, such as, for example, dichloromethane, carbon tetrachloride, benzene, xylene, chlorobenzene, chloroform, methylene chloride, pentane, iso-octane, decalin, etc. Preferred solvents include the aliphatic and alicyclic hydrocarbons and their chlorinated derivatives such as cyclohexane, etc. In general, any suitable solvent that is either inert or substantially inert under the reaction conditions such that it does not react with the reactants to any substantial extent is useful within the purview of this invention.

In the reduction process the temperature is from −20° to 100° C., preferably from 0° to 50° C. The sodium sulfite reducing agent is preferably used in the form of a concentrated aqueous solution. An inert organic solvent such as a chlorinated hydrocarbon is used as a solvent for the N-chloro-N-(4-chlorocrotyl-1) compound to be reduced. The reduction is effected while the reaction mixture is vigorously stirred. The reduction usually requires several hours. The completion of the reaction is usually established using a potassium iodide test for the disappearance of the N-chloro group.

As previously noted, the N-chlorocrotyl compounds of this invention are useful as pesticides. One aspect of such pesticidal application is as a herbicide, preferably as post-emergent, or as a fungicide. When used as a fungicide or herbicide, the compositions of this invention may be used to control plant growth or fungi thereon either applying to foliage or plant growth media, a growth- or fungi-controlling dosage of the present acyl compound or of concentrated compositions prepared from many of the aforesaid compounds (as an active ingredient) in intimate admixture with at least one material of the group consisting of finely divided inert solids, granular solids, surface active dispersing agents, beeswax, paraffin waxes, water, organic solvents, nitrogen fertilizers, potassium fertilizers, meta phosphates, etc. Particularly contemplated as desirable concentrate compositions are those which comprise the aforesaid novel chlorocrotyl compounds of this invention as active ingredients in an intimate admixture with at least one material of the group consisting of finely divided solids, inert granular solids, and surface active dispersing agents.

The expression "surface active dispersing agent" as herein employed is intended to include all agents which are capable of acting at the interfacial surface between the aforesaid carbamate derivative or composition and water or organic solvents as the dispersion dispersant media, facilitating thereby the dispersion of the toxicant in water or organic solvents to form aqueous and emulsified concentrate. The term is inclusive of solid emulsifying agents such as finely divided bentonite, pyrophyllite, fuller's earth, attapulgite, silica, other clays and mineral carriers, as well as liquid and solid ionic and non-ionic wetting and dispersing agents, alkaline metal caseinates, alkyl aryl sulfonates, sulfonated oils, complex organic ester derivatives, condensation products of alkene alkaline oxides and organic acids, mahogany soaps, etc.

Other suitable surface active dispersing agents may be found in "Detergents and Emulsifiers, Up to Date", written and published by John W. McCutcheon, Inc., New York, 1962.

The term "finely divided inert solids" as herein employed refers to material whose primary function is not as dispersant of the present N-chlorocrotyl derivatives in water or organic solvents, but as carrier for dust compositions. Illustrative of such carriers are materials such as chalk, talc, gypsum, etc.

The term "inert granular solids" refers to mineral or other inert carriers which are suitable for dry application and which include corn cobs, sand, and other materials which differ primarily in particle size from the "finely divided inert solids".

According to the present invention, any of the appropriate crotyl derivatives disclosed herein may be compounded with any of the finely divided solids to form dust compositions by grinding, mixing, or wetting the finely divided carrier with a solution of the toxicant and a volatile organic solvent. Similarly, dust compositions containing the aforesaid carbamate derivatives may be compounded from any one or more of the solid surface active dispersing agents previously mentioned, such as bentonite, fuller's earth, attapulgite, and other clays. Depending upon the proportions of ingredients, these dust mixtures may be employed either as treating compositions or as concentrates to be subsequently diluted with additional solid surface active dispersing agent or with talc, chalk, gypsum, etc., to obtain the desired amount of toxicant in a composition adapted to be applied to plants, plant growth media, or fungi thereon, for the suppression of plant growth or said fungi. Also, such concentrate dust compositions may be dispersed in water or organic solvent with or without the aid of additional dispersing or emulsifying agent to form spray mixtures.

Dust concentrates, such as above-described, or, alternatively, appropriate crotyl derivative compounds may be intimately mixed with liquid or solid ionic or non-ionic dispersing agents to form spray concentrates. Such concentrates are readily dispersible in liquid carriers to form sprays containing the crotyl derivative in any desired amount.

Any of the above crotyl compounds of this invention may also be compounded with suitable water-miscible or water-immiscible organic liquid and surface active dispersing agents, provided that they do not react with the N-chlorocrotyl compounds, to produce liquid concentrates which may be further formulated with water and/or oil to prepare spray mixtures in the form of aqueous dispersions or oil-in-water emulsion compositions. The exact step to be employed in preparing such compositions is within the knowledge of those skilled in the art. Preferred water-immiscible organic liquids include petroleum oil and distillates, toluene, xylene, cumene and other aromatic hydrocarbon solvents, chlorinated aliphatic hydrocarbons, isoparaffin oil and other aliphatic hydrocarbon solvents.

When the aforesaid crotyl derivatives of this invention are alkali metal, ammonium, or amine salts, aqueous concentrate compositions are readily prepared. The salts may be first compounded in a water-miscible organic solvent and added to a minimal amount of water, or they may be directly compounded in water or in a water-organic solvent mixture. Usually the use of a procedure which includes addition of a small amount of a water-miscible organic solvent is preferred. Moreover, in the case of salt compositions, the salt need not be performed but may be prepared during the compounding process. Thus, the desired N-chlorocrotyl compound and desired amine or inorganic base may be mixed together in appropriate amounts in an aqueous organic solvent mixture.

The present composition may also contain other plant growth modifying agents either as adjuvants or supplementary materials for both terrestrial and equetic applications.

In carrying out the methods of the present invention, as they pertain to the growth control of fungi or of plant growth or vegetation, the crotyl derivatives of this invention are administered to foliage, plant parts, or growth media of the plant species whose pesticide control is desired. The exact amount to be administered varies with the particular type of growth control to be achieved. It further varies with method of application, i.e., whether the application is to be made to foliage, food, flower, or particular plant part, or to soil or other growth media, and the overall site of application: a sheltered area, such as a greenhouse; or an exposed area, such as fields, etc. Thus, as for example, in the treatment of grass and weeds, soil application is preferred to foliage application and the amounts are governed thereby. Also, weeds present in sheltered areas are more responsive to treatment and minimal dosages are usually adequate whereas field applications often times require higher dosages to counteract adverse weather effect. An additional factor to be considered is the plant species to be treated, as well as the presence or absence of desirable plants together with the undesirable species. Thus, selective grass control may be achieved by administering sufficient N-chlorocrotyl derivatives of this invention to eradicate grasses without affecting broad base leaf.

Effective control of terrestrial plants in soil may be readily achieved by the administration of various N-chlorocrotyl derivatives of this invention.

The administration of the present compounds or compositions thereof to plant or plant growth media may be carried out in any manner known to those skilled in the art and may be carried out by using dust compositions, sprays, or any other modification provided that an effective dosage is supplied. It is to be understood that the total volume or weight of the treating composition to be employed is not critical so long as the critical amount of the aforesaid crotyl compound is supplied, which is, in the present instance, about 0.5 to 50 pounds per acre.

Frequently, the desirability of a more concentrated or dilute composition depends upon a method of application and the area to be covered; hence, the selection of the concentration and total volume or weight may be made by those of ordinary skill in the art in view of the foregoing teachings.

The present invention is further illustrated in greater detail by the following examples, but it is to be understood that the present invention, in its broadest aspects, is not necessarily limited in terms of the specific temperatures, residence times, reactants, pressures, solvents, analytical techniques, separation techniques, and other process conditions by which the compounds and compositions described and claimed in this invention are prepared and used.

EXAMPLE 1

The Addition of N,N-Dichloro Methyl Carbamate to Conjugated Dienes

The N,N-dichloro methyl carbamate was added dropwise to a stirred nitrogen purged solution of an equimolar amount of conjugated diene in methylene chloride solution cooled to between $-10°$ and $-20°$ C. by a dry ice-isopropanol bath. The rate of addition of the carbamate was such that the internal temperature was maintained between $-10°$ and $0°$ C. After addition was complete the reaction mixture was allowed to warm to room temperature. The solvent was removed at aspirator pressure at ambient temperature to yield the crude product as an oil. The product was then purified by vacuum distillation.

The results obtained using this procedure or its converse, i.e., adding the conjugated diene to a solution of the N,N-dichloro methyl carbamate in methylene chloride solution, are summarized in Table I.

TABLE I

PREPARATION OF N-CHLORO-N-(4-CHLOROCROTYL) METHYL CARBAMATES $$CH_3OCNCl_2 + \underset{R_3 \ \ R_4 \ R_5 \ \ R_7}{\overset{R \diagdown \ \ \ \ \ \diagup R_6}{C=C-C=C}} \longrightarrow CH_3OCN-\underset{Cl \ \ R_3 \ R_4 \ R_5 \ R_7}{\overset{R_2 \ \ \ \ \ R_6}{C-C=C-C}}-Cl$$

| $R_2,R_3,R_4,R_5,R_6,R_7$ | % Yield | b.p.° C.(mm) | $N_D^{23}$ | Adduct % by 1,2 | Isomers, nmr, 1,4 | C% Calcd | C% Found | H% Calcd | H% Found | N% Calcd | N% Found |
|---|---|---|---|---|---|---|---|---|---|---|---|
| H, H, H, H, H, H | 91 | 52–6(0.005) | 1.4930 | 14 | 86 | 36.38 | 36.27 | 4.58 | 4.73 | 7.07 | 6.98 |
| H, H, CH$_3$,H, H, H | 82 | 72–4(0.065) | 1.4964 | | 85(a) | 39.64 | 39.55 | 5.23 | 5.35 | 6.60 | 6.63 |
| H, H, CH$_3$, CH$_3$, H, H | 80 | 83 (0.006) | 1.4996 | | 100 | 42.49 | 42.41 | 5.80 | 5.99 | 6.19 | 6.12 |
| H, H, Cl, H, H, H | 82 | 78 (0.003) | 1.5095 | | 100 | 30.99 | 31.06 | 3.47 | 3.90 | 6.02 | 6.05 |
| H, H, H, H, H, CH$_3$ | 84 | 65 (0.01) | 1.4852 | 27 | 73(b) | 39.64 | 39.28 | 5.23 | 5.32 | 6.60 | 6.23 |

(a)15% 4,1-addition.
(b)40% 4,1-addition; 33% 4,1-addition

EXAMPLE 2

The Addition of N,N-Dichloro Methyl Carbamate to 1,3-Butadiene 1,3-Butadiene (54 g, 1.0 mole) was diluted with nitrogen and slowly passed with stirring into 140 g (0.98 mole) of N,N-dichloro methyl carbamate cooled to $-10°$ C. by a dry ice-acetone bath. The rate of addition was such that the internal temperature was maintained between 5° and 10° C. After addition was complete the reaction was warmed slowly to room temperature. The yield of product was 192 g. A gc analysis indicated a purity of 98% and a 90:10 ratio of 1,4- to 1,2-adducts.

EXAMPLE 3

The Addition of N,N-Dichloro Methyl Carbamate to 1,3-Butadiene 1,3-Butadiene (5.4 g, 0.1 mole) was diluted with nitrogen and passed into a stirred solution of 14.2 g (0.1 mole) of N,N-dichloro methyl carbamate in 35 ml of benzene cooled by an ice water bath. The rate of addition was adjusted to maintain the internal temperature between 5° and 10° C. After addition was complete the solution was slowly warmed to room temperature. The benzene was evaporated to yield 19.6 g of oil. A gc analysis indicates a 90:10 ratio of 1,4- to 1,2-adducts. Analysis by nmr indicates a 88:12 ratio of the same adducts.

EXAMPLE 4

The Addition of N,N-Dichloro Isopropyl Carbamate to Butadiene-1,3

1,3-Butadiene (10.6 g, 0.2 mole) was diluted with nitrogen and passed into 34.0 g (0.2 mole) of N,N-dichloroisopropyl carbamate cooled to $-10°$ C. by a dry ice-acetone bath. The rate of addition of diene was adjusted so as to maintain the internal temperature between 5° and 10° C. After addition was complete the reaction was warmed slowly to room temperature. The product weighed 43.2 g. A gc analysis showed an 89:11 ratio of 1,4- to 1,2-adducts and a purity of 98%. The product was purified by vacuum distillation to give an 85% yield of adduct, b.p. 75°–7° C. (0.006 mm), $n_D^{23}$ 1.4762. Calcd. for $C_8H_{13}Cl_2NO_2$: C, 42.49; H, 5.80; N, 6.20. Found: C, 42.53; H, 5.85; N, 6.32.

EXAMPLE 5

The Addition of N,N-Dichloro Isopropyl Carbamate to Isoprene

Isoprene (10.2 g, 0.15 mole) was added dropwise with stirring to a nitrogen purged solution of 25.8 g (0.15 mole) of N,N-dichloro isopropyl carbamate in 25 ml of methylene chloride solution cooled to $-10°$ C. The rate of addition was such that the internal temperature was maintained between 0° and 5° C. After addition was completed, the reaction was slowly warmed to room temperature. The solvent was evaporated to give 36 g. of crude product. Distillation gave a 94% yield of mono adduct b.p. 85°–7° C. (0.007 mm), $n_D^{23}$ 1.4814. An examination of the nmr spectrum of this mono adduct indicated that the material consisted of an 85:15 mixture of 1,4- and 4,1-adducts. Calcd. for $C_9H_{15}Cl_2NO$: C, 52.55; H, 7.84; N, 6.81. Found: C, 55.32; H, 8.16; N, 6.81.

EXAMPLE 6

The Addition of N,N-Dichloro Isopropyl Carbamate to 2,3-Dimethyl-1,3-Butadiene The reaction 0.08 mole of N,N-dichloro isopropyl carbamate with 0.08 mole of 2,3-dimethyl-1,3-butadiene using the above procedure gave 15.4 g (0.065 mole, 82%) of N-chloro-N-2,3-dimethyl-4-chlorobut-2-ene-(1) isopropyl carbamate b.p. 81°–3° C. (0.005 mm), $n_D^{23}$ 1.4850. Calcd. for $C_{10}H_{17}Cl_2NO_2$: C, 47.25; H, 6.75; N, 5.51. Found: C, 47.30; H, 7.06; N, 5.30.

EXAMPLE 7

The Addition of N,N,N',N'-Tetrachloro Ethylene Glycol Bis Carbamate to Chloroprene A solution of 9.8 g (0.034 mole) of N,N,N',N'-tetrachloro ethylene glycol bis carbamate in 15 ml of methylene chloride solution was added dropwise with stirring to a solution of 6.1 g (0.068 mole) of freshly distilled chloroprene in 15 ml of methylene chloride cooled to $-20°$ C. in a dry ice-acetone bath. The rate of addition was such that the internal temperature remained below $-10°$ C. After addition was complete the reaction was warmed slowly to room temperature and the solvent evaporated to yield 15.8 g of oily adduct. The material was homogeneous on tlc. The nmr indicated exclusive 1,4-addition with a small amount of methylene chloride as the chief contaminants. A sample was stored under high vacuum at room temperature for 15 hours and then submitted for elemental analysis. Calcd. for $C_6H_7Cl_3NO_2$: C, 31.12; H, 3.05; N, 6.05. Found: C, 30.74; H, 3.25; N, 6.08.

EXAMPLE 8

The Addition of N,N,N',N'-Tetrachloro Ethylene Glycol Bis Carbamate to 1,3-Butadiene The reaction was performed as described in Example 3 to give 73 g. of adduct as an oil from 53.6 g of N,N,N',N'-tetrachloro ethylene glycol bis carbamate. An nmr spectrum of this material indicated that it consisted of an 85:15 mixture of 1,4- and 1,2-adducts. Calcd. for $C_6H_8Cl_2NO_2$: N, 7.11. Found: N, 7.14.

EXAMPLE 9

General Procedure for the Reduction of N-Chloro-N[4-chlorocrotyl-(1)] Carbamates A solution of N-chloro-N-[4-chlorocrotyl-(1)] carbamate in methylene chloride was vigorously stirred at ambient temperature with an aqueous solution of a three-fold excess of sodium sulfite until the organic layer failed to give a positive potassium iodide test. The layers were separated and the methylene chloride phase was washed with water and dried over anhydrous potassium carbonate. The methylene chloride was evaporated at ambient temperature to yield the reduced product as a liquid or solid which was then purified by the appropriate method. The results are listed in Table II.

TABLE II

REDUCTION OF N-CHLORO-N-CROTYL CARBAMATES WITH SODIUM SULFITE $$R_1OCN-R_2 + Na_2SO_3 \longrightarrow R_1OCNHR_2$$
$$\phantom{xxx}\underset{Cl}{|}$$

| $R_1O-\overset{O}{\overset{\|}{C}}-NH-R_2$ | | Yield, % | m.p. (b.p.), °C |
|---|---|---|---|
| $R_1$ | $R_2$ | | |
| $CH_3$ | $CH_2-CH=CH-CH_2Cl$ | 89 | 31–3° |
| $CH_3$ | $CH_2-\underset{\underset{CH_3}{\|}}{C}=CH-CH_2Cl$ | 76 | 31–2° |
| $CH_3$ | $CH_2-\underset{\underset{Cl}{\|}}{C}=CH-CH_2Cl$ | 78 | 58–9° |
| $CH_3$ | $CH_2-\underset{\underset{CH_3}{\|}}{C}=\underset{\underset{CH_3}{\|}}{C}-CH_2Cl$ | 84 | 52–3° |

TABLE II-continued
REDUCTION OF N-CHLORO-N-CROTYL CARBAMATES WITH SODIUM SULFITE $$R_1OCN(Cl)-R_2 + Na_2SO_3 \rightarrow R_1OCNHR_2$$

$$R_1O-\underset{O}{\overset{\|}{C}}-NH-R_2$$

| $R_1$ | $R_2$ | Yield, % | m.p. (b.p.), °C. |
|---|---|---|---|
| $CH_3$ | $\begin{Bmatrix} CH-CH=CH-CH_2-Cl \\ \quad \mid \\ \quad CH_3 \\ CH_2-CH=CH-CH-Cl \\ \qquad\qquad\qquad \mid \\ \qquad\qquad\qquad CH_3 \end{Bmatrix}$ | 82 | (84–6° 90.004 mm) |
| $i\text{-}C_3H_7$ | $CH_2-CH=CH-CH_2Cl$ | 78 | 61-2° |
| $i\text{-}C_3H_7$ | $CH_2-\underset{\underset{CH_3}{\mid}}{C}=CH-CH_2Cl$ | 81 | 51-2° |

EXAMPLE 10
The Addition of N,N-Dichloro Benzenesulfonamide to 1,3-Butadiene 1,3-Butadiene (1.6 g, 0.03 mole) was diluted with nitrogen and slowly distilled into a stirred solution of N,N-dichloro benzenesulfonamide (5.9 g, 0.026 mole) in 15 ml of methylene chloride cooled to −10° C. by a dry ice-isopropanol bath. The rate of addition was such that the internal temperature of the reaction remained between 0° and 5°. After addition was complete the reaction mixture was allowed to slowly come to room temperature. The solvent was removed at ambient temperature at aspirator pressure to give 7.4 g of oil which solidified on standing. Recrystallization from a carbon tetrachloride-pentane mixture gave 5.7 g (76%) of 1,4-adduct m.p. 53°-5° C.

EXAMPLE 11
The Addition of N,N-Dichloro Methanesulfonamide to Chloroprene A solution of 30.0 g (0.183 mole) of N,N-dichloro methanesulfonamide in 75 ml of methylene chloride was added dropwise to a stirred solution of 16.2 g (0.183 mole) of chloroprene in 50 ml of methylene chloride and cooled to −20° C. in a dry ice-isopropanol bath. The rate of addition was controlled so that the internal temperature of the reaction mixture remained between −10° and 0° C. After addition was complete the reaction mixture was allowed to slowly come to room temperature. The solvent was removed at aspirator pressure to yield 46 g of solid. Recrystallization from carbon tetrachloride gave 41.1 g (89%) of 1,4-adduct m.p. 70°-2° C.

EXAMPLE 12
Addition of N,N-Dichloro Sulfonamides to Conjugated Dienes in General N,N-dichlorobenzene sulfonamide-4-chlorobenzene sulfonamide, and methane sulfonamide were reacted with butadiene and chloroprene in a manner described in Example 5.

Pertinent data regarding the preparation of the resulting N-chloro-N-crotyl sulfonamides are given in Table III.

TABLE III
PREPARATION OF N-CHLORO-N-CROTYL SULFONAMIDES $$R''SO_2NCl_2 + CH_2=\underset{\underset{X}{\mid}}{C}-CH=CH_2 \longrightarrow R''SO_2N\underset{\underset{Cl}{\mid}}{CH_2}-\underset{\underset{X}{\mid}}{C}=CHCH_2Cl$$

| R'' | X | % Yield | m.p. °C. |
|---|---|---|---|
| $C_6H_5$ | H | 76 | 53–5 |
| $C_6H_5$ | Cl | 90 | 51–2 |
| $pCl-C_6H_4$ | H | 85 | 126–7 |
| $pCl-C_6H_4$ | Cl | 85 | 87–8 |
| $CH_3$ | H | 85 | 52—3 |
| $CH_3$ | Cl | 89 | 70–2 |

Satisfactory elemental analyses were obtained on all adducts.

EXAMPLE 13
General Procedure for the Reduction of N,N-Dichloro Sulfonamide-Conjugated Diene Adducts A solution of adduct in methylene chloride was vigorously stirred at room temperature with an aqueous solution containing a threefold excess of sodium sulfite until the organic layer failed to give a positive potassium iodide test. The organic layer was separated, dried over sodium sulfate, filtered and evaporated to give the reduced product which was then purified by recrystallization. Pertinent data regarding the reduction of N-chloro-N-crotyl sulfonamides are given in Table IV.

TABLE IV
REDUCTION OF N-CHLORO-N-CROTYL SULFONAMIDES $$R''SO_2N\underset{\underset{Cl}{\mid}}{CH_2}-\underset{\underset{X}{\mid}}{C}=CHCH_2Cl \xrightarrow{Na_2SO_3} R''SO_2NHCH_2\underset{\underset{X}{\mid}}{C}=CHCH_2Cl$$

| R'' | X | % Yield | m.p. °C. |
|---|---|---|---|
| $C_6H_5$ | H | 82 | Oil |
| $C_6H_5$ | Cl | 80 | 83–4 |
| $pClC_6H_4$ | H | 78 | 78–9 |
| $pClC_6H_4$ | Cl | 78 | 81–2 |
| $CH_3$ | H | 82 | 26–7 |
| $CH_3$ | Cl | 85 | 57–8 |

Satisfactory elemental analyses were obtained on all reduction products.

EXAMPLE 14

Addition of N,N-Dichloro-N',N'-Dimethylsulfamide to Chloroprene treated soil eight of the cotton plants survived even though they were inoculated with Pythium sp. In contrast, in the untreated but inoculated soil, none of the cotton plants survived.

TABLE V

SOIL FUNGICIDAL ACTIVITY OF N-CHLORO-N-CROTYL CARBAMATES AND REDUCED DERIVATIVES

| Reference | Structure | % Conc. | Soil | **Number of Plants Surviv. | | |
|---|---|---|---|---|---|---|
| | | | | Cotton | Cucumber | Tomato |
| Table I | $CH_3OCN(Cl)-CH_2CH=CH-CH_2Cl$ (O=) | 0.5<br>0.5 | Inoc.*<br>Uninoc.* | 8<br>9 | 9<br>10 | 11<br>16 |
| Table II | $CH_3OCNHCH_2CH=CH-CH_2Cl$ (O=) | 0.5 | Inoc.<br>Uninoc. | 9<br>9 | 10<br>10 | 6<br>20 |
| Table III | $CH_3OCNHCH_2C(CH_3)=CHCH_2Cl$ (O=) | 0.1 | Inoc.<br>Uninoc. | 0<br>8 | 6<br>7 | 17<br>18 |
| Untreated | | —<br>— | Inoc.<br>Uninoc. | 0<br>8 | 0<br>9 | 6<br>16 |

*Inoculated
Uninoculated
**Each flat both inoculated and uninoculated was seeded with cotton, 10 cucumber and 20 tomato seeds.

A solution of 12.2 g (0.063 mole) of N,N-dichloro-N',N'-dimethylsulfamide in 50 ml of methylene chloride was added dropwise to a stirred solution of 5.6 g (0.063 mole) of freshly distilled chloroprene in 25 ml of methylene chloride cooled to −15° C. by a dry ice isopropanol bath. The rate of addition was regulated so that the internal temperature remained between −10° and 5° C. After addition was complete the reaction was warmed slowly to room temperature and the solvent evaporated to yield an oil. The oil was dissolved in carbon tetrachloride and pentane was added to the cloud point. Upon cooling 15.0 g, 84%, of 1,4-adduct m.p. 36°–8° C. crystallized. An analytical sample had a m.p. 38°–40° C. Anal. Calcd. for $C_6H_{11}Cl_3N_2O_2S$: C, 25.59; H, 3.94; N, 9.95; S, 11.39. Found: C, 25.64; H, 3.91; N, 10.65; S, 11.46.

EXAMPLE 15

Use of N-Chloro-N-Crotyl Carbamates and Their Reduction Products as Soil Fungicides Using standard techniques both the N,N-dichloro methyl carbamate-1,3-butadiene adduct and its reduced derivative were screened by the Wisconsin Alumni Research Foundation as soil fungicides. The test organism used for cucumbers was Pythium sp., for cotton, Rhizoctonia solani and for tomatoes, Fusarium oxysporum. The data obtained are listed in Table V.

The data showed that both the adduct and its reduced derivative show a fungicidal effect. For example, in the case of the N,N-dichloro methyl carbamate adduct

EXAMPLE 16

Use of N-Chloro-N-Crotyl Carbamates and Their Reduction Products on Herbicides

Samples of unknown activity are tested at a concentration equivalent to 20 lbs. per acre. Atrazine and 2,4-D are used as positive standards.

Pre-emergence tests — Duplicate paper pots filled with a soil mixture are seeded with snap beans, cotton, corn, wheat, mustard, pigweed, crabgrass and foxtail. Immediately after seeding the soil is sprayed with the sample solution. Growth occurs under artificial light with overhead irrigation. The plants are observed for about ten days and an injury rating is given in comparison with untreated controls.

Post-emergence tests — Duplicate paper pots filled with vermiculite are seeded with the same plants employed in the pre-emergence tests. Growth occurs under artificial light with irrigation provided by placing the porous pots in a small amount of water in stainless steel trays. After about ten days when the test plants reach a suitable size they are sprayed with the sample. Observations are made for ten days and an injury rating is given in comparison with untreated controls.

The results are shown in Table VI. The data show that although the N-chlorocrotyl carbamates of the present invention are not active as pre-emergence herbicides, they are highly active as post-emergence herbicides when used at a concentration of 0.5% which is equivalent to 20 lbs. per acre.

TABLE VI

POST-EMERGENCE HERBICIDAL TEST DATA FOR N-CHLORO-N-CROTYL CARBAMATES AND THEIR REDUCTION PRODUCTS

| Reference Table | Structure | Conc. %(a) | Mustard Pre | Mustard Post | Pigweed Pre | Pigweed Post | Crab-Grass Pre | Crab-Grass Post | Foxtail Pre | Foxtail Post | Corn Pre | Corn Post | Wheat Pre | Wheat Post | Cotton Pre | Cotton Post | Beans Pre | Beans Post |
|---|---|---|---|---|---|---|---|---|---|---|---|---|---|---|---|---|---|---|
| I | $CH_3OCN(Cl)CH_2CH=CHCH_2Cl$ $\parallel$ $O$ | 0.5 0.5 | 0 0 | 5G 4W | 0 0 | 5G 5W | 0 0 | 5T 5W | 0 0 | 3T 1L | 0 0 | 4T 1L | 0 0 | 3T 1L | 0 0 | 4G | 0 0 | 4G 2U |
| II | $CH_3OCNHCH_2CH=CHCH_2Cl$ $\parallel$ $O$ | 0.5 | 0 | 5G 4W | 0 | 5G 5W | 0 | 4T 2W | 0 | 3T 1L | 0 | 5T 3W | 0 | 3T 1L | 0 | 4G | 0 | 3G 3U |
| I | $CH_3OCNCl_2 + CH_2=CHCH=CHCH_3$ $\parallel$ $O$ | 0.5 | 0 | 4G 4W | 0 | 5G 4W | 0 | 3T 2L | 0 | 3T 2L | 0 | 2L 2T | 0 | 2L 2T | 0 | 3L 1S | 0 | 2L 2G |
| I | $CH_3OCN(Cl)CH_2C(CH_3)=CCH_3$ $\parallel\qquad\qquad\quad\mid$ $O\qquad\qquad\quad CH_2Cl$ | 0.5 | 0 | 4G 4N | 0 | 5G 5W | 0 | 3T 2L | 0 | 4T 2L | 0 | 4T 3W | 0 | 2L 2T | 0 | 2L,1S 3G | 0 | 3L 2G |
| II | $CH_3OCNHCH_2C(CH_3)=CHCH_2Cl$ $\parallel$ $O$ | 0.5 | 0 | 2G 1L | 0 | 4G 4W | 0 | 2T 2L | 0 | 2T 2L | 0 | 2T 1L | 0 | 2L 2T | 0 | 2L 1S | 0 | 3L 2G |
| Untreated | | 0 | 0 | 0 | 0 | 0 | 0 | 0 | 0 | 0 | 0 | 0 | 0 | 0 | 0 | 0 | 0 | 0 |

Legend - Degree of Injury
0 - none    3 - moderately severe
1 - slight    4 - severe
2 - moderate    5 - death Type of Injury
C - Chlorosis    NG - No Growth    TB - Terminal Bud
E - Epinasty    R - Reduction    U - Leaf Curl Upward
G - General Necrosis    RG - Reduced Germination    W - Wilting
H - Hypertrophy    S - Stunting
L - Local Necrosis    SS - Stem Swelling
M - Mottled    SC - Stem Curling
NF - Nodule Formation    T - Tip Burn (a) 0.5% concentration corresponds to a rate of approx. 20 lbs. acre.

EXAMPLE 17

Use of N-Chloro-N-Crotyl Sulfonamides as Soil Fungicides

The N,N-dichloro methyl sulfonamide-chloroprene adduct was screened by the Boyce Thompson Institute for Plant Research Inc. as a soil fungicide. The following procedure was used.

Separate lots of sterilized soil were inoculated with Pythium, Fusarium, and Rhizoctonia. The inoculated soil was placed in 4 oz. dixie cups and 2 to 5 days later the cups were drenched with 30 ml of a formulation containing sufficient chemicals to give a dose rate of 50 lbs./acre or 25 ppm in the soil. The treated cups were incubated for two days at 70° F. The amount of mycelial growth on the soil surface was then rated on a scale of 1–5, where 1 = no control and 5 = complete control of mycelial growth.

The mycelial growths on Pythium, Fusarium and Rhizoctonia were rated 5, 4, 3 indicating from complete to substantial control.

It will be understood that the foregoing description is merely illustrative of preferred embodiments and specific examples of the present invention and that variations may be made in such embodiments and examples by those skilled in the art without departing from the spirit and purview thereof.

What is claimed is:

1. A selective addition process for the preparation of N-chloro-N-(4-chlorocrotyl-1) sulfonamides comprising reacting a $C_1$ to $C_{30}$ N,N-dichlorosulfonamide with a $C_4$ to $C_{30}$ conjugated diene at a temperature between about −80° and about 100° C. in the liquid phase.

2. A selective reduction process for the preparation of N-(4-chlorocrotyl-1) sulfonamides comprising reacting an N,N-dichloro compound selected from the group consisting of $C_1$ to $C_{30}$ N-chloro-N-(4-chlorocrotyl-1) sulfonamide with sodium sulfite at a temperature of from −20° to 100° C.

3. A selective addition-reduction process for the preparation of N-(4-chlorocrotyl-1) acyl compounds comprising adding an N,N-dichloro acyl compound of the formula R"SO₂NCl₂ wherein R" is a hydrocarbyl radical having from 1 to 30 carbon atoms and is selected from the group consisting of unsubstituted alkyl and substituted alkyl to a conjugated diene of from 4 to 30 carbon atoms of the formula

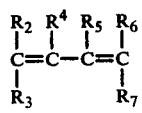

wherein $R_2$ to $R_7$ are selected from the group consisting of hydrogen, chlorine, fluorine, and alkyl groups having from 1 to 30 carbon atoms at a temperature of between −80° and about 100° C. in the absence of added catalyst and at pressures between about 1 and about 10 atmospheres in the liquid phase to obtain a major amount of an adduct of the formula

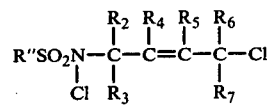

and reducing the N-chloro group of said adduct with sodium sulfite at a temperature of between about −20° to about 100° C.

4. A selective addition process for the preparation of N-chloro-N-(4-chlorocrotyl-1) acyl compounds comprising adding an N,N-dichloroacyl compound of the formula R"SO₂NCl₂ wherein R" is a hydrocarbyl radical having from 1 to 30 carbon atoms and is selected from the group consisting of unsubstituted alkyl and substituted alkyl to a conjugated diene of from 4 to 30 carbon atoms of the formula

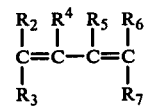

wherein $R_2$ to $R_7$ are selected from the group consisting of hydrogen, chlorine, fluorine and alkyl groups having from 1 to 30 carbon atoms at a temperature of between −80° and about 100° C. in the absence of added catalyst and at pressures between about 1 and about 10 atmospheres in the liquid phase to obtain a major amount of an adduct of the formula

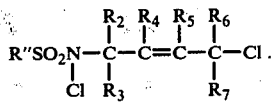

5. A selective reduction process for the preparation of N-(4-chlorocrotyl-1) acyl compounds comprising reacting compounds of the formula

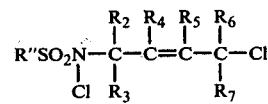

wherein R" is a hydrocarbyl radical having from 1 to 30 carbon atoms and is selected from the group consisting of unsubstituted and substituted alkyl and $R_2$ and $R_7$ are selected from the group consisting of hydrogen, chlorine, fluorine and alkyl groups having from 1 to 30 carbon atoms and combinations thereof with sodium sulfite at a temperature of from about −20° to about 100° C.

6. The process of claim 3 wherein the substituent on the substituted $C_1$ to $C_{30}$ alkyl group comprising the R" group is selected from the group consisting of chloro, nitro and phenyl.

7. The process of claim 4 wherein the substituent on the substituted $C_1$ to $C_{30}$ alkyl group comprising the R" group is selected from the group consisting of chloro, nitro and phenyl.

8. The process of claim 5 wherein the substituent on the substituted $C_1$ to $C_{30}$ alkyl group comprising the R"

group is selected from the group consisting of chloro, nitro and phenyl.

9. N-chlorocrotyl sulfonamide compositions of the formula

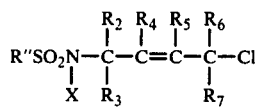

wherein R'' is a hydrocarbyl radical having from 1 to 30 carbon atoms and is selected from the group consisting of unsubstituted alkyl and substituted alkyl, $R_2$ to $R_7$ are selected from the group consisting of hydrogen, chlorine, fluorine and alkyl groups having from 1 to 30 carbon atoms and combinations thereof and X is selected from the group consisting of chlorine and hydrogen.

10. N-chlorocrotyl sulfonamide compositions of the formula

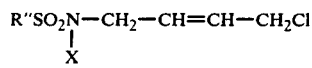

wherein R'' is a $C_1$ to $C_{30}$ hydrocarbyl radical selected from the group consisting of unsubstituted alkyl and substituted alkyl and X is selected from the group consisting of chlorine and hydrogen.

11. The composition of claim 9 wherein the substituent on the substituted $C_1$ to $C_{30}$ alkyl group comprising the R'' group is selected from the group consisting of chloro, nitro and phenyl.

12. The composition of claim 10 wherein the substituent on the substituted $C_1$ to $C_{30}$ alkyl group comprising the R'' group is selected from the group consisting of chloro, nitro and phenyl.

13. N-[4-chlorocrotyl-(1)] benzene sulfonamide and N-chloro derivative thereof.

14. N-[4-chlorocrotyl-(1)] methane sulfonamide and N-chloro derivative thereof.

15. N-[2,4-dichlorocrotyl-(1)] N,N'-dimethyl sulfamide and N-chloro derivative thereof.

16. N-chloro-N-[2,4-dichlorocrotyl-(1)] methane sulfonamide.

17. A selective addition process for the preparation of N-chloro-N-[2,4-dichlorocrotyl-(1)] methane sulfonamide comprising reacting N,N-dichloro methane sulfonamide with chloroprene at a temperature of between about −80° and about 100° C. in the liquid phase.

* * * * *